US006267114B1

(12) United States Patent
Ueno

(10) Patent No.: US 6,267,114 B1
(45) Date of Patent: Jul. 31, 2001

(54) HANDY OXYGEN GENERATOR

(75) Inventor: Shinji Ueno, Kumamoto (JP)

(73) Assignee: Hoshiko Inc., Tokyo (JP)

( * ) Notice: Subject to any disclaimer, the term of this patent is extended or adjusted under 35 U.S.C. 154(b) by 0 days.

(21) Appl. No.: 09/311,344

(22) Filed: May 13, 1999

(30) Foreign Application Priority Data

May 14, 1998 (JP) ..... 10-150702
Nov. 6, 1998 (JP) ..... 10-331935

(51) Int. Cl.[7] ..... A61M 15/00
(52) U.S. Cl. ..... 128/202.26; 128/200.24; 128/202.25; 128/205.21
(58) Field of Search ..... 128/200.24, 202.25, 128/202.26, 205.27, 205.21, 201.13

(56) References Cited

U.S. PATENT DOCUMENTS

| | | | | |
|---|---|---|---|---|
| 3,574,561 | * | 4/1971 | Nickerson et al. | 422/106 |
| 3,955,931 | * | 5/1976 | Thompson | 128/202.26 |
| 3,971,372 | * | 7/1976 | Lenk et al. | 128/202.26 |
| 4,278,637 | * | 7/1981 | MCbreide | 128/202.26 |
| 4,491,130 | * | 1/1985 | Pasternack | 128/202.26 |
| 5,535,736 | * | 7/1996 | Jzaw | 128/202.26 |
| 5,804,146 | * | 9/1998 | Hyer et al. | 128/202.26 |

FOREIGN PATENT DOCUMENTS

| | | | | |
|---|---|---|---|---|
| 0107471 A2 | * | 5/1984 | (EP) | 128/202.26 |
| 0254314 A2 | * | 1/1988 | (EP) | 128/202.26 |
| 2133698 | * | 8/1984 | (GB) | 128/202.26 |
| 2134504 | * | 8/1984 | (GB) | 128/202.26 |
| 6-47236 | | 1/1989 | (JP) . | |
| 4-40650 | | 4/1992 | (JP) . | |
| 4-154603 | | 5/1992 | (JP) . | |
| 4-32002 | | 5/1992 | (JP) . | |
| 6-107401 | | 4/1994 | (JP) . | |

* cited by examiner

*Primary Examiner*—Dennis Ruhl
*Assistant Examiner*—Virendra K Srivastava
(74) *Attorney, Agent, or Firm*—Wenderoth, Lind & Ponack, L.L.P.

(57) ABSTRACT

A handy oxygen generator containing an oxygen generating agent which reacts with water to evolve oxygen can arbitrarily supply plenty of oxygen under all circumstances at any time. The oxygen generator can be efficiently used particularly in life-threatening emergencies such as a fire and other accidents or when climbing a mountain or playing a sport. The oxygen generator may be formed of a sealed container partitioned into two chambers separately containing water and the oxygen generating agent, so that the separately contained oxygen generating agent and water can be mixed to react with each other by easily breaking the partition with an external pressure force. The oxygen generator containing beforehand the water along with the oxygen generating agent is very convenient to carry because it has no need of procuring water.

25 Claims, 4 Drawing Sheets

HANDY OXYGEN GENERATOR

BACKGROUND OF THE INVENTION

1. Field of the Invention

This invention relates to an improvement in an oxygen generating device, and more particularly to a disposable oxygen generator which is easy to carry and handle and can be suitably used for supplying oxygen in life-threatening emergencies such as a fire and other various accidents or when climbing a mountain or playing a sport.

2. Description of the Prior Art

In general, there has been known an oxygen generator capable of generating oxygen by decomposing peroxide or an adduct of sodium carbonate peroxide used as an oxygen generating agent with catalysts or oxygen in the presence of water. (e.g. Japanese U.M. Appln. Public Disclosures SHO 64-7236(A) and HEI 4-40650(A) and Japanese Patent Appln. Pub. Disclosure HEI 1-17620(A))

Also, a portable oxygen generator formed by a small steel can filled with compressed oxygen, which is also "oxygen can", has been on the market. Thus, every conventional oxygen generator is generally made by a rigid cylindrical can container of plastic or steel. Accordingly, even though the conventional oxygen generators of this type must be made for the purpose of carrying convenience, they are bulky and heavy, and thus, inconvenient to carry about.

The steel can container of the conventional portable oxygen generator can contain only several liters of oxygen at the most. Thus, when a large quantity of oxygen is required, a number of oxygen generators must be prepared and carried. As a result, the whole of the oxygen generators of a required number becomes unduly large, cumbersome and very expensive. Furthermore, the conventional portable oxygen generator entailed a disadvantage such that it is restricted in usage because, for instance, ICAO and IATA prohibit passengers on an airplane from carrying such a resultantly cumbersome oxygen generator into the airplane.

There has been a great need for a handy oxygen generator made serviceably compact for carrying convenience and capable of immediately supplying oxygen particularly in life-threatening emergencies such as a fire and other various accidents or when climbing a mountain or playing a sport.

OBJECT OF THE INVENTION

An object of the present invention is to provide a safe and handy oxygen generator made lightweight and compact for carrying and storing convenience, which can generate oxygen with a simple operation as plenty as need be.

Another object of the invention is to provide a portable oxygen generator serviceable enough for various purposes of not only giving oxygen to, for example, a sufferer who meets with an accident such as a fire and suffers from oxygen starvation or a patient who has a fit attributable to cardiopulmonary malfunctions or shows other symptoms, to save the patient's life, but also supplying oxygen for a climber, sports player, heavy worker or the like.

Still another object of the invention is to provide a safe, handy oxygen generator capable of effectively evolving oxygen even in a state of violent vibration or its inverted posture, which is allowed to be carried in an airplane.

SUMMARY OF THE INVENTION

To attain the objects described above according to the present invention, there is provided a handy oxygen generator comprising a sealed container having an oxygen discharge nozzle, and an oxygen generating agent for generating oxygen by reacting with water introduced into the sealed container.

The oxygen generated by the reaction between the water introduced into the sealed container and the oxygen generating agent contained in the sealed container can be discharged out of the sealed container through the oxygen discharge nozzle according to demand.

The water to react with the oxygen generating agent to bring forth the required oxygen may be introduced from the outside of the sealed container into the container. In this case, the sealed container of the oxygen generator may be formed of an inner reaction bag and an outer sealing bag in a double-ply construction. In this double-ply sealed container, it is desirable to dispose the oxygen discharge nozzle on the outer sealing bag, and have the inner reaction bag made of a flexible sheet material or membrane having not only watertightness and water repellent, but also gas permeability, so as to allow only oxygen to pass therethrough. In addition, the container is provided with a water introducing tube penetrating the outer and inner bags so as to open at its one end on the outside of the outer sealing bag and at the other end on the inside of the inner reaction bag. Through the water introducing tube, the water can be introduced into the gas-permeable inner reaction bag. The water introducing tube is ordinarily kept covered with removable closing means such as a lid or cap, and opened when introducing the water into the inner reaction bag. Since the oxygen generator made of the flexible inner and outer bags as noted above can fold up into a small size, it is very convenient to carry about.

Upon introducing the water into the inner reaction bag having gas permeability through the water introducing tube to evolve oxygen as the result of making the oxygen generating agent contained in the inner reaction bag react with the water introduced into the inner reaction bag, the water introducing tube is closed with the closing means to fill the inner reaction bag with the oxygen thus produced, consequently to allow the oxygen produced in the gas-permeable inner reaction bag to pass through the gas-permeable inner reaction bag. The oxygen produced in the gas-permeable inner reaction bag is allowed to pass through the gas-permeable inner reaction bag, but prevented from passing through the outer sealing bag. Although the oxygen passes through the gas-permeable inner reaction bag, the water and the oxygen generating agent contained in the inner reaction bag are prevented from flowing out through the gas-permeable inner reaction bag having watertightness. As a result, the oxygen is entrapped in a space between the gas-permeable inner reaction bag and the outer sealing bag, and then, flows out of the space between the inner and outer bags through the oxygen discharge nozzle to be placed into service for oxygen inhalation or the like.

The inner reaction bag is made of a flexible sheet having both watertightness and gas permeability, such as a membrane of polypropylene plastic or fluorine plastic, or by laminating such a watertight, gas-permeable sheet or membrane with reinforcing fibrous or unwoven fabric material.

As the oxygen generating agent to generate oxygen by reacting with water, there may be used an adduct of sodium carbonate peroxide or urea peroxide, or solid peroxide such as of sodium perborate. The oxygen generating efficiency of the oxygen generating agent can be increased by adding thereto a reaction accelerator such as a catalyst of manganese dioxide or rare metal, and catalase enzyme.

The water may be previously contained in the sealed container of the oxygen generator along with the oxygen generating agent so that the oxygen generating agent can be made to react with the water as needed. In this case, the sealed container may be divided into a water chamber and an agent chamber by a partition means capable of being easily broken by a relatively small pressure force imparted externally, so that the water and the oxygen generating agent are isolated from each other in the container when kept unused and come in contact with each other by breaking the partition means by the pressure force imparted externally to the sealed container from outside in use. By mixing the water and the oxygen generating agent in the sealed container, the oxygen generating agent is made to react with the water to produce the required oxygen. The oxygen discharge nozzle on the sealed container, from which is emitted the oxygen evolved as the result of making the oxygen generating agent react with the water, may be stuffed with a breathing member having both watertightness and gas permeability. The watertight and gas-permeable breathing member placed within the oxygen discharge nozzle can prevent leakage of the water and oxygen generating agent contained in the container, but permits only the oxygen produced to be emitted through the oxygen discharge nozzle, even when using the oxygen generator in any posture.

The breathing member in the oxygen discharge nozzle may be made of a watertight and gas-permeable membrane such as of polypropylene plastic or fluorine plastic, or by laminating such a watertight, gas-permeable sheet or membrane with reinforcing fibrous or unwoven fabric material.

It is desirable to close the oxygen discharge nozzle with removable closing means such as a lid or cap when the oxygen generator is not in use, so that the oxygen generator can be carried about. It is convenient to fold the oxygen generator in two so as to put the divided water and agent chambers on top of each other when being carried or stored.

Other and further objects of this invention will become obvious upon an understanding of the illustrative embodiments about to be described or will be indicated in the appended claims, and various advantages not referred to herein will occur to one skilled in the art upon employment of the invention in practice.

DESCRIPTION OF THE PREFERRED EMBODIMENTS

Figure 1:
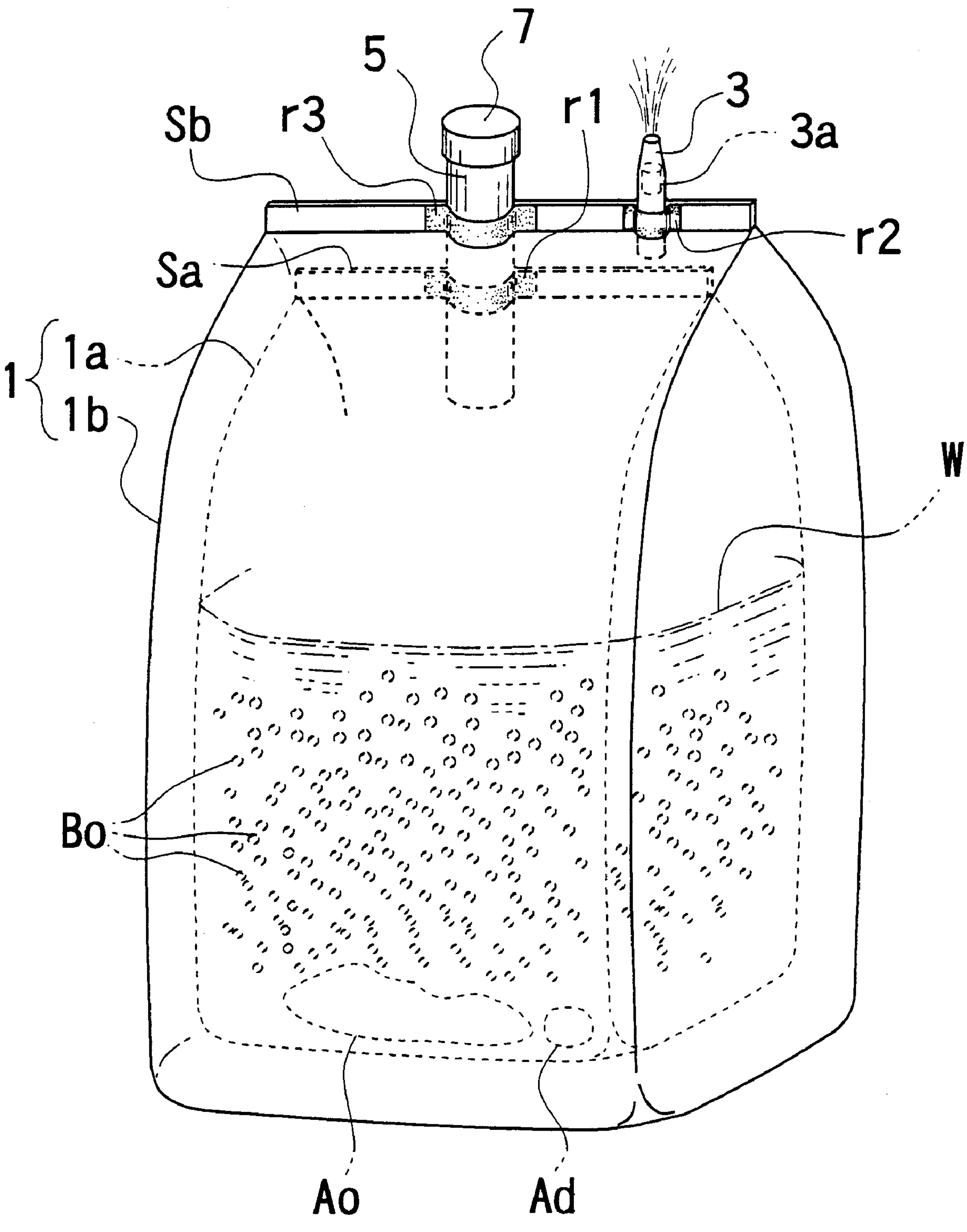
FIG. 1 is a schematic perspective view showing a first embodiment of a handy oxygen generator according to this invention.

Referring to FIG. 1 showing the first embodiment of the invention, the handy oxygen generator according to this invention comprises a sealed container 1 of a double-ply construction of an inner reaction bag 1*a* and an outer sealing bag 1*b*, an oxygen discharge nozzle 3 penetrating the outer sealing bag 1*b*, and an oxygen generating agent Ao for generating oxygen by reacting with water W introduced into the inner reaction bag 1*a*.

The oxygen generator in this first embodiment is provided with a water introducing tube 5 penetrating the inner reaction bag 1*a* and the outer sealing bag 1*b* so as to have one end open to the outside of the outer sealing bag 1*b* and the other end open to the inside of the inner reaction bag 1*a* to introduce the water W into the inner reaction bag 1*a*.

The inner reaction bag 1*a* is made of a flexible sheet material or membrane having not only watertightness and water repellent, but also gas permeability so as to allow only gas to pass therethrough.

For example, the watertight and gas-permeable inner reaction bag 1*a* may be formed by making a polypropylene or fluorine plastic sheet or membrane porous so as to allow oxygen molecules to pass therethrough (gas-permeability), but prevent water molecules from passing therethrough (watertightness). It is desirable to further laminate such a porous sheet or membrane with reinforcing fibrous or unwoven fabric material.

The porous sheet or membrane may be formed by making uncounted numbers of so exceedingly minute holes or pores in the plastic sheet as to allow the oxygen molecules to pass therethrough, but prevent the water molecules from passing therethrough.

As the watertight and gas-permeable materials, there have been known sheet materials used for sanitary items, paper diapers or the like. Also, Gore-Tex™ made by Japan Gore-Tex Inc., which has both watertightness and gas-permeability, has been known. Of course, it is possible to apply any other desired materials having both watertightness and gas-permeability to this invention.

The watertight and gas-permeable sheet may be preferably lined with reinforcing fibrous or unwoven fabric material to remarkably increase its strength.

The watertight and gas-permeable sheet of the inner reaction bag 1*a* may be made by other methods. For example, it can be obtained by stretching extruded film of polyethylene compound mixed with fine powder of calcium carbonate to form a porous gas-permeable membrane having exceedingly minute holes or pores. It is desirable to cover the porous gas-permeable membrane thus obtained with reinforcing fibrous or unwoven fabric material.

The inner reaction bag 1*a* may be formed by doubling or folding the watertight and gas-permeable sheet or butt-contacting two or more watertight and gas-permeable sheets with the reinforcing fibrous or unwoven fabric material layer or layers placed outside, and airtightly welding the peripheral edge portion or portions thereof by heating or other suitable method.

When heat-welding the watertight and gas-permeable sheets into a bag shape as illustrated, the water introducing tube 5 is interposed between the sheets at an appropriate position of the edge portion thereof to be secured to the inner reaction bag. In this embodiment, the water introducing tube 5 is placed on the upper seal portion Sa of the inner reaction bag 1*a*. It is desirable to securely mount the water introducing tube 5 to the inner reaction bag 1*a* with a strengthening seal member r1 as shown in FIG. 1.

The outer sealing bag 1*b* is larger in size than the inner reaction bag 1*b* so as to enclose the inner reaction bag 1*b*. The outer sealing bag 1*b* is made of a tough, flexible sheet material having excellent waterproofness and airtightness. As the sheet material suitable therefor, for instance, a plastic film such as of polyethylene resin, polypropylene resin, or vinyl resin, or a paper or other sheet material laminated with a plastic film or aluminum foil may be used.

The outer sealing bag 1*b* is formed into a bag shape by doubling or folding the waterproof, airtight sheet thus obtained or butt-contacting two or more waterproof, airtight sheets, and airtightly welding the peripheral edge portion or portions thereof by heating or other suitable method. When forming or shaping the outer sealing bag 1*b,* the oxygen discharge nozzle 3 and the water introducing tube 5 are interposed between the waterproof sheets at an appropriate position of the edge portion thereof to be secured to the outer sealing bag. In this embodiment, the oxygen discharge nozzle 3 and the water introducing tube 5 are placed on the upper seal portion Sb. It is desirable to securely mount the oxygen discharge nozzle 3 and the water introducing tube 5 to the outer sealing bag 1*b* with strengthening seal members r2 and r3 as illustrated.

The oxygen discharge nozzle 3 is used for discharging the oxygen collected in between the inner reaction bag 1*a* and the outer sealing bag 1*b*. The oxygen discharge nozzle 3 has a size and diameter suitable for being easily taken in the mouth of a user. That is, the oxygen generated in the oxygen generator of the invention is generally sucked directly by the user through the oxygen discharge nozzle 3, but may be provided another apparatus or system by use of another connecting tube connected to the oxygen discharge nozzle.

Thus, the shape and size of the oxygen discharge nozzle 3 may be determined at discretion or in accordance with the purpose for which the oxygen generator of the invention is used.

Within the oxygen discharge nozzle 3, there may be placed a filter 3*a* for allowing the oxygen to pass therethrough and preventing passing of moisture mist, waterdrops or other undesirable substances which may possibly be produced in the outer sealing bag 1*b*. The filter 3*a* placed in the oxygen discharge nozzle 3 may be composed of an air-permeable sponge layer and/or an activated charcoal layer. It is convenient to make the filter 3*a* exchangeable so that it can be used sanitarily.

The water introducing tube 5 for pouring water into the sealed inner reaction bag 1*a* may be formed of a tube or cylindrical member having a round or elliptical section and made of relatively rigid and thin material such as vinyl chloride resin, or soft material such as polyethylene.

The water introducing tube 5 is ordinarily closed with closing means 7 such as a lid or cap capable of being removably screwed on or snap-fastened to the outer opening of the water introducing tube 5. As another measure for forming the closing means 7 capable of opening and closing the water introducing tube 5, an on-off valve or tap may be disposed on the water introducing tube. Or, a pressure-sealing zip-fastener for blocking up the water introducing tube 5 may be integrally formed with the outer sealing bag 1*b*. Owing to the closing means 7, it is possible to supply or exchange contents such as the water W and the oxygen generating agent Ao in the inner reaction bag 1*a* and prevent the contents in the inner reaction bag 1*a* from leaking out even when the oxygen generator is carried by hand or stored. The closing means 7 is easily removable so as to supply or exchange the contents in the inner reaction bag 1*a* with ease.

As the oxygen generating agent Ao to be contained in the inner reaction bag 1*a,* there may be used, for example, an adduct of sodium carbonate peroxide or urea peroxide, or solid peroxide such as of sodium perborate. However, the oxygen generating agent applied to this invention is by no means limited only to these components.

It is a matter of course that enhancement of the oxygen generating efficiency of the oxygen generating agent Ao is desirable. For the purpose of improving the oxygen generating efficiency of the agent, it is preferable to add a decomposition agent or reaction accelerating agent Ad to the oxygen generating agent Ao. As the decomposition agent Ad, there may be used a catalyst of manganese dioxide or rare metal, or catalase enzyme. However, the decomposition agent Ad being applicable to this invention is by no means limited only to these components.

Next, a method by which one of the oxygen generators were produced actually according to this invention by way of experiment to substantiate the excellent effects brought about by the invention will be described.

First, a transparent sealed container 1 was made by inserting an inner bag 1*a* having a capacity of about 300 ml into an outer bag 1*b* made of a low-density polyethylene film of 10 $\mu$m in thickness and having a capacity of about 500 ml. Then, a water introducing tube 5 of low-density polyethylene and having an outer diameter of 14 mm, a thickness of 1 mm and a length of 60 mm was provided on the sealed container 1. The water introducing tube 5 was closed with a screw cap of low-density polyethylene, which served as closing means 7.

On the way of producing the sealed container 1, the sealing performance of the inner bag 1*a* having the aforementioned structure was experimentally verified in the following manner.

That is, the inner bag 1 was filled with water to about 70% of its capacity, and shaken hard vertically and horizontally in its normal and inverted postures with the water introducing tube 5 closed with the screw cap 7. However, no leakage of water was found.

Besides, a functional test for verifying the airtight performance of the sealed container 1 and gas-permeability of the inner bag 1*a* was carried out by high-pressure air in the following manner.

That is, upon formation of the sealed container 1 by inserting the inner bag 1*a* into the outer bag 1*b* and sealing them together by heat, air pressure of about 0.3 Kgf/cm 2 in gauge pressure was applied into the inner bag 1*a* and subsequently into the outer bag 1*b* with the oxygen discharge nozzle 3 closed. When the air pressure was introduced into the inner bag 1*a,* air was emitted from the oxygen discharge nozzle 3, thus proving that the gas-permeability of the inner bag 1*a* is sufficient. When the air pressure was further applied to the outer bag 1*b,* no leakage of air from the outer bag 1*b* was found, thus proving that the airtightness of the outer bag 1*b* is perfect.

After carrying out the aforementioned functional test, dry air was continuously fed via the water introducing tube 5 into the sealed container 1 having the oxygen discharge nozzle 3 and water introducing tube 5 kept open approximately all day and night, to completely dry the insides of the inner and outer bags 1*a* and 1*b*. Thereafter, an oxygen generating agent Ao was introduced into the inner bag 1*a*.

In the experiment, upon containing 100 g of a dried adduct of sodium carbonate peroxide as the oxygen generating agent Ao and 0.5 g of granulated catalase enzyme as the decomposition agent Ad into the inner bag 1*a,* the inner and outer bags 1*a* and 1*b* were sealed airtightly.

The oxygen discharge nozzle 3 in the oxygen generator was made of a low-density polyethylene pipe having a thickness of 2 mm and an outer diameter of 6 mm. The oxygen discharge nozzle 3 in the experiment was provided with a tapered end portion so as to be easily connected to a silicone rubber tube used as an attachment of the nozzle 3. A cartridge of filter 3*a* composed of an air-permeable sponge layer and/or an activated charcoal layer was placed in the oxygen discharge nozzle 3.

After removing the cap 7 from the water introducing tube 5 of the oxygen generator made by way of experiment, 250 ml of water was introduced into the inner bag 1*a* through the water introducing tube 5 to fill the inner bag 1*a* about half full of water, and then, the water introducing tube 5 was immediately closed with the cap 7. Right after introducing the water into the inner bag, a reaction of the oxygen generating agent Ao with the water with the aid of the decomposition agent Ad took place. As a result, vigorous generation of bubbles Bo could be observed through the transparent sealed container 1, to thus swell the inner bag 1*a*. Gas discharged from the inner bag 1*a* through the oxygen discharge nozzle 3 was recognized as 100% pure oxygen by measurement.

The high-purity oxygen generated from the oxygen generating agent Ao deposited on the bottom of the inner bag 1*a* was collected in the upper portion of the inner bag 1*a* and vigorously discharged from the oxygen discharge nozzle 3 at a flow rate of 1.5 liters per minute for 6 minutes.

During evolution of the oxygen in the inner bag 1*a,* the sealed container 1 was laid on its side, turned upside down and shaken violently as an experiment. However, the sealed container 1 exhibited no leakage of water, oxygen or any other contents, and thereafter, the oxygen was stably discharged from the oxygen discharge nozzle 3.

As is apparent from the foregoing disclosure, the oxygen generator according to this invention is handy and convenient to carry and store and easy to handle and fulfills an excellent function of sufficiently and stably supplying pure oxygen over a long time as needed with a simple operation of pouring water into the inner bag 1*a* to make the oxygen generating agent Ao contained in the inner bag 1*a* generate oxygen.

Although the water W to react with the oxygen generating agent Ao is introduced from the outside of the sealed container 1 into the inner bag 1*a* in the first embodiment noted above, it may be contained beforehand in the sealed container in the following manner.

The second embodiment of the invention, which will be disclosed hereinafter, dispenses with the necessity of removing the lid cap 7 from the water introducing tube 5, pouring a necessary quantity of water into the sealed container and again closing the water introducing tube 5 with the lid cap 7.

Figure 2:
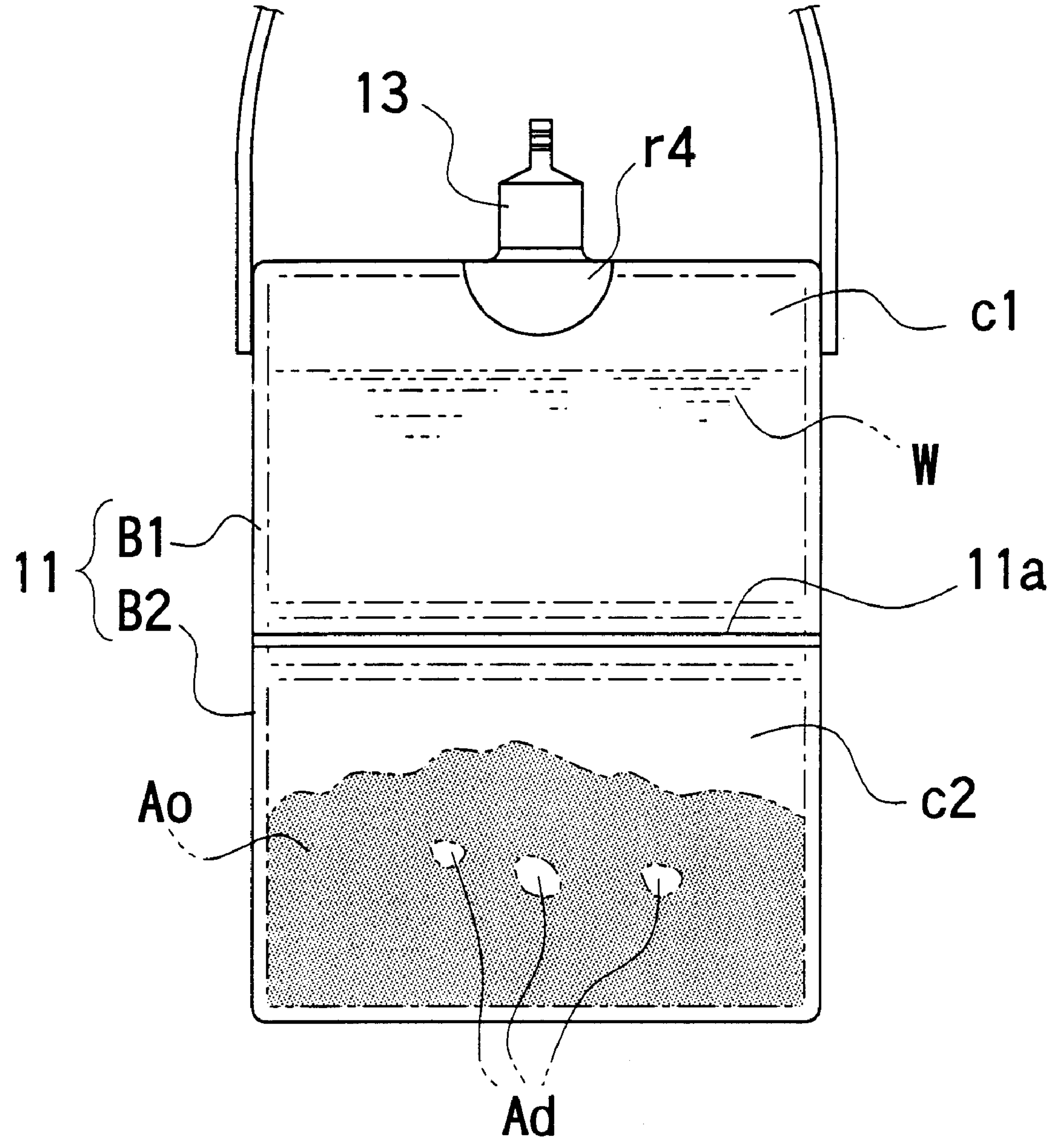
FIG. 2 is a schematic perspective view showing a second embodiment of the handy oxygen generator according to this invention.
Figure 3:
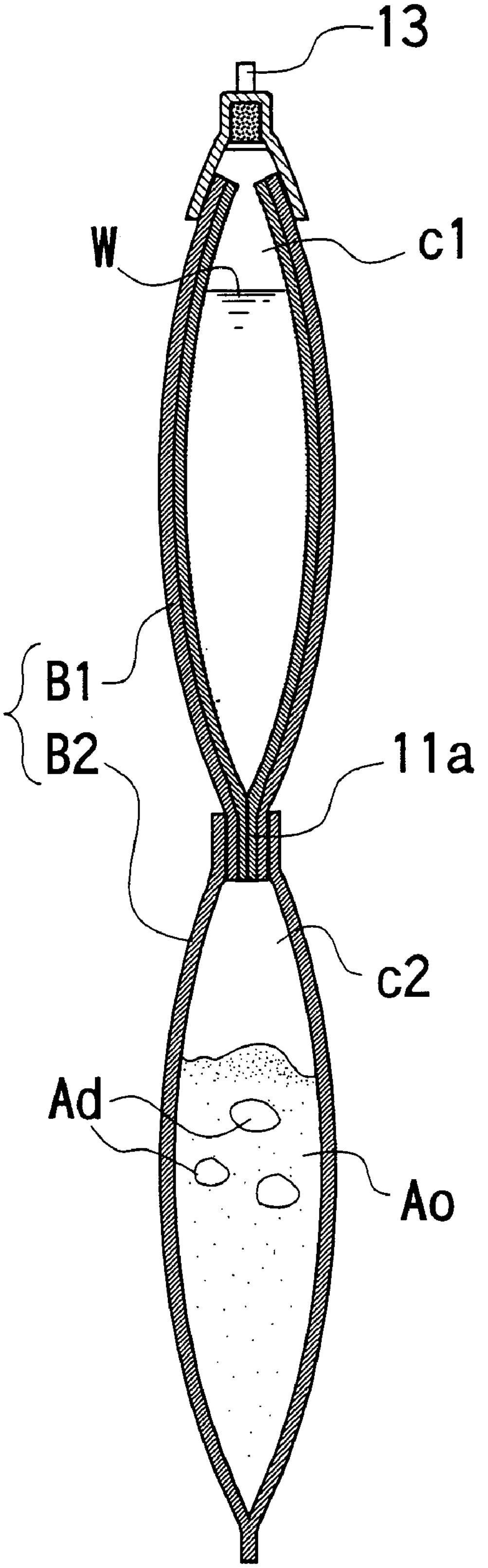
FIG. 3 is a schematic side section of the oxygen generator of FIG. 2.

That is, as shown in FIG. 2 and FIG. 3, the oxygen generator of the second embodiment comprises a sealed container 11 having two chambers C1 and C2 for separately containing water W and an oxygen generating agent Ao. Namely, the inner space in the sealed container 11 is divided into the water chamber C1 for the water W and an agent chamber C2 for the oxygen generating agent Ad by a partition means 11*a*. The partition means 11*a* can easily be broken by a relatively small external pressure force, so that the water W and the oxygen generating agent Ao are isolated from each other in the container when kept unused and come in contact with each other by breaking the partition means 11*a* by the external pressure force imparted to the sealed container from outside in use.

The sealed container 11 may be made by forming a plastic film or membrane such as of polyethylene resin, polypropylene resin, or vinyl resin, or a paper or sheet material laminated with a plastic film or aluminum foil to ensure watertightness and airtightness into a bag shape by heat-welding or other bonding method.

The partition means 11*a* may be made by heat-welding the substantially center part horizontally traversing the sealed container 11 or formed of a pressure-sealing zip-fastener at the substantially center part of the sealed container. Or, there may be adopted a structure for tightly sealing the substantially center part of the sealed container 11 by folding the sealed container 11 into two with pressure and breaking the seal by spreading the folded container to mix the oxygen generating agent and water both contained in the sealed container 11. In any case, the partition means 11*a* may be formed so as to be easily broken or come off by a simple operation.

By breaking or tearing off the partition means 11*a,* the oxygen generating agent Ao and the water W are mixed to generate oxygen.

The sealed container 11 in the second embodiment shown in FIG. 3 comprises a first bag member B1 having the water chamber C1 for containing the water W and a second bag member B2 having the oxygen generating chamber C2 for the oxygen generating agent Ao. The first and second bag members B1 and B2 are united by heat-welding. When heat-welding, the partition means 11*a* is formed and the oxygen discharge nozzle 13 is put between the films or membranes constituting the first bag member B1. It is desirable to attach a strengthening seal member r4 to the first bag member B1 to strengthen the bag member around the oxygen discharge nozzle 13, as illustrated.

Figure 4:
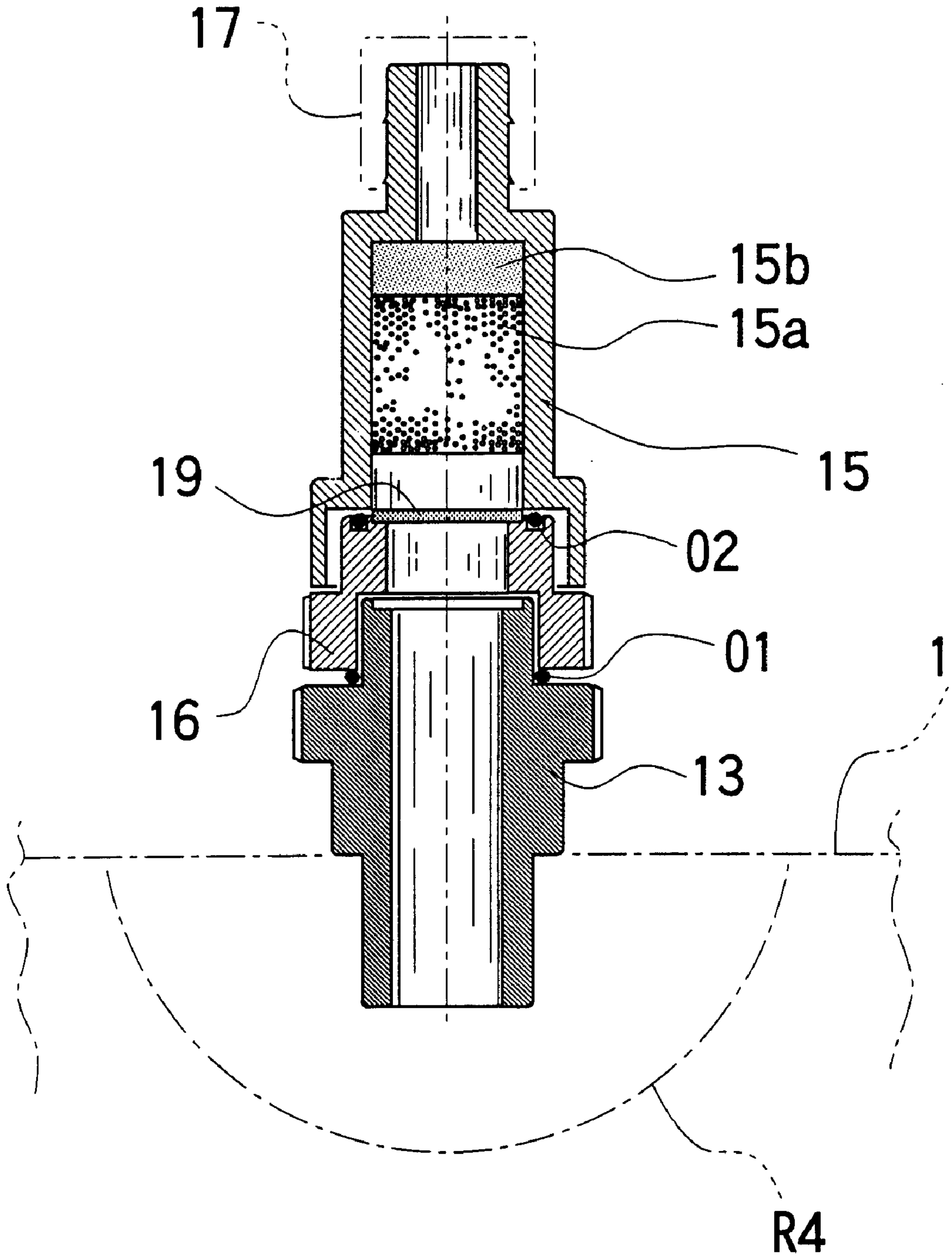
FIG. 4 is a side section showing an oxygen discharge nozzle in the oxygen generator of FIG. 2.

Similarly to the first embodiment described above, the oxygen discharge nozzle 13 for discharging the oxygen collected in the sealed container 11 may have a size and diameter suitable for being easily taken in the mouth of a user. However, the oxygen discharge nozzle 13 may be connected to an attachment 15 containing an activated charcoal layer 15*a* and a filter 15*b,* as illustrated in FIG. 4. Although the oxygen discharge nozzle 13 in the illustrated embodiment is connected to the attachment 15 through a connection ring 16, the connection ring 16 is not always necessary and may be omitted or screwed directly onto the attachment 15. The opening of the attachment 15 may be closed with appropriate closing means such as a cap 17.

In the illustrated embodiment, between the attachment 15 and the connection ring 16 is placed a filter 19 having watertightness and gas permeability. The watertight and gas-permeable filter 19 may be formed by making so minute holes or pores as to allow the oxygen molecules to pass therethrough (gas-permeability), but prevent the water molecules from passing therethrough (watertightness) in a plastic film or sheet such as of polypropylene, polyethylene, vinyl resin and fluorine resin or fibrous or unwoven fabric material. As the watertight and gas-permeable filter, Gore-Tex™ made by Japan Gore-Tex Inc. may be used.

Between the oxygen discharge nozzle 13 and the connection ring 16 and between the connection ring 16 and the attachment 15, there are placed O-rings O1 and O2, respectively.

The same oxygen generating agent Ao and reaction accelerating agent Ad as used in the first embodiment described above may be adopted in this second embodiment.

The oxygen generator of the second embodiment can be produced in various ways. As one example, it may be produced by beforehand preparing the first bag member B1 and second bag member B2 constituting the sealed container 11, placing the oxygen generating agent Ao and reaction accelerating agent Ad in the second bag member B2, uniting the second bag member B2 with the first bag member B1 by heat-welding or other bonding method, placing the water W in the first bag member B1, and finally, sealing the first bag member B1 with the oxygen discharge nozzle 13 interposed between the films or membranes constituting the first bag member B1. When uniting the second bag member B2 with the first bag member B1, the partition means 11*a* is formed.

Although the water W is enclosed in the first bag member B1 before sealing the first bag member B1, it may be poured into the sealed container 11 at any time.

For example, the water W may be introduced into the first bag member B1 immediately before the oxygen generator is used. That is, after introducing the water W into the first bag member B1 and closing the oxygen discharge nozzle 13 with the closing means 17, an external pressure force is imparted to the sealed container 11 to break the partition means 11*a*, so that the water W and the oxygen generating agent Ao are mixed together, consequently to generate oxygen.

However, by beforehand containing the water W in the first bag member B1, the oxygen generator of the invention can be conveniently used without procuring water. Thus, the oxygen generator of this embodiment is very convenient to carry and can be freely used anywhere at any time because the components necessary for generating the oxygen, i.e. water W, oxygen generating agent Ao and so on, are contained beforehand in the oxygen generator and can easily be mixed by breaking the partition means 11*a* with a small pressure force imparted to the oxygen generator.

Some oxygen generators of the aforementioned second embodiment according to the invention were actually produced by way of experiment, as a result of which its excellent function of efficiently generating oxygen could be verified.

One of the oxygen generators experimentally produced contains about 250 ml of water W in the water chamber C1 of the sealed container 11, and 100 g of sodium carbonate peroxide adduct as the oxygen generating agent Ao together with 0.5 g of granulated catalase enzyme as the decomposition agent Ad for accelerating the reaction in the agent chamber C2. In the experiment, the partition means 1*a* formed between the water chamber C1 and the agent chamber C2 was broken by exerting pressure on a part of the sealed container 11 containing the aforementioned components to mix the water W and the oxygen generating agent Ao. Consequently, a vigorous reaction set in with a rapid evolution of oxygen. The oxygen was discharged from the oxygen discharge nozzle 13 at a flow rate of 1.5 liters per minute for 8 minutes at an average.

During evolution of the oxygen in the inner bag 11*a*, the sealed container 11 was laid on its side, turned upside down and shaken violently in every direction as an experiment. However, the sealed container 11 did not leak water, oxygen or any other contents, and thereafter, the oxygen was stably discharged from the oxygen discharge nozzle 13.

As described above, the oxygen generator according to this invention is lightweight, compact for carrying and storing convenience and can stably evoke oxygen with a simple operation as plenty as need be. Furthermore, the oxygen generator of the invention is serviceable enough for various purposes of not only giving oxygen to, for example, a sufferer who meets with an accident such as a fire and suffers from oxygen starvation or a patient who has a fit attributable to cardiopulmonary malfunctions or shows other symptoms, to save the patient's life, but also supplying oxygen for a climber, sports player, heavy worker or the like. Since the oxygen generator of the invention is formed of tough sheet material so as not to cause leakage of oxygen and water, it is so safe as to be permitted to be carried in an airplane.

As can be readily appreciated, it is possible to deviate from the above embodiments of the present invention and, as will be readily understood by those skilled in this art, the invention is capable of many modifications and improvements within the scope and spirit thereof. Accordingly, it will be understood that the invention is not to be limited by these specific embodiments, but only by the scope and spirit of the appended claims.

What is claimed is:

1. A handy oxygen generator comprising a sealed container having an oxygen discharge nozzle, and an oxygen generating agent contained in said sealed container for generating oxygen by reacting with water introduced into said sealed container, wherein said sealed container comprises an inner reaction bag made of a flexible sheet material or membrane having watertightness to prevent water from passing therethrough and gas permeability to allow oxygen to pass therethrough, an outer sealing bag made of a flexible sheet material or membrane having watertightness, and a water introducing tube penetrating said outer and inner bags for introducing water into said inner reaction bag, said oxygen discharge nozzle penetrating said outer sealing bag for discharging oxygen collected in between said outer sealing bag and said inner reaction bag.

2. A handy oxygen generator according to claim 1, wherein said inner reaction bag is made of a flexible gas-permeable sheet of polypropylene plastic or fluorine plastic.

3. A handy oxygen generator according to claim 1, wherein said inner reaction bag is made by laminating a flexible gas-permeable sheet of polypropylene plastic or fluorine plastic with reinforcing fibrous or unwoven fabric material.

4. A handy oxygen generator according to claim 1, wherein said oxygen generating agent is sodium carbonate peroxide, urea peroxide, or solid peroxide of sodium perborate.

5. A handy oxygen generator according to claim 1, wherein a reaction accelerator consisting of a catalyst of manganese dioxide or rare metal, or catalase enzyme is added to said oxygen generating agent.

6. A handy oxygen generator according to claim 1, wherein said oxygen generating agent is sodium carbonate peroxide, urea peroxide, or solid peroxide of sodium perborate, and a reaction accelerator consisting of a catalyst of manganese dioxide or rare metal, or catalase enzyme is added to said oxygen generating agent.

7. A handy oxygen generator according to claim 1, wherein said outer sealing bag is made of a plastic film of polyethylene resin, polypropylene resin, or vinyl resin, or a paper or plastic sheet laminated with a plastic film or aluminum foil.

8. A handy oxygen generator according to claim 1, wherein said inner reaction bag is made of a flexible gas-permeable sheet of polypropylene plastic or fluorine plastic, and said outer sealing bag is made of a plastic film of polyethylene resin, polypropylene resin, or vinyl resin.

9. A handy oxygen generator according to claim 1, wherein said inner reaction bag is made of a flexible gas-permeable sheet of polypropylene plastic or fluorine plastic, and said outer sealing bag is made of a paper or plastic sheet laminated with a plastic film or aluminum foil.

10. A handy oxygen generator according to claim 1, wherein said water introducing tube is closed with removable closing means.

11. A handy oxygen generator according to claim 1, wherein said oxygen discharge nozzle is provided therewithin with a filter for allowing only oxygen generated in said sealed container to pass therethrough, said filter being filled with an air-permeable sponge layer and/or an activated charcoal layer.

12. A handy oxygen generator according to claim 1, wherein said sealed container is divided into a water chamber for containing water and an agent chamber for containing said oxygen generating agent by a partition to isolate said water in said water chamber from said oxygen generating agent in said agent chamber, and allow said water and oxygen generating agent to come into contact with each other by breaking said partition by an external pressure force imparted to said sealed container.

13. A handy oxygen generator according to claim 1, wherein said sealed container is divided into a water chamber for water and an agent chamber for containing said oxygen generating agent and a reaction accelerating agent by a partition to isolate said water in said water chamber from said oxygen generating agent in said agent chamber, and allow said water and oxygen generating agent to come into contact with each other by breaking said partition by an external pressure force imparted to said sealed container.

14. A handy oxygen generator according to claim 13, wherein said inner reaction bag is made of a flexible gas-permeable sheet of polypropylene plastic or fluorine plastic.

15. A handy oxygen generator according to claim 13, wherein said inner reaction bag is made by laminating a flexible gas-permeable sheet of polypropylene plastic or fluorine plastic with reinforcing fibrous or unwoven fabric material.

16. A handy oxygen generator according to claim 13, wherein said oxygen generating agent is sodium carbonate peroxide, urea peroxide, or solid peroxide of sodium perborate.

17. A handy oxygen generator according to claim 13, wherein a reaction accelerator consisting of a catalyst of manganese dioxide or rare metal, or catalase enzyme is added to said oxygen generating agent.

18. A handy oxygen generator according to claim 13, wherein said oxygen generating agent is sodium carbonate peroxide, urea peroxide, or solid peroxide of sodium perborate, and a reaction accelerator consisting of a catalyst of manganese dioxide or rare metal, or catalase enzyme is added to said oxygen generating agent.

19. A handy oxygen generator according to claim 13, wherein said outer sealing bag is made of a plastic film of polyethylene resin, polypropylene resin, or vinyl resin.

20. A handy oxygen generator according to claim 13 wherein said outer sealing bag is made of a paper or plastic sheet laminated with a plastic film or aluminum foil.

21. A handy oxygen generator according to claim 13, wherein said water introducing tube is closed with a removable closing device.

22. A handy oxygen generator according to claim 13, wherein said oxygen discharge nozzle is provided therewithin with a filter for allowing only oxygen generated in said sealed container to pass therethrough, said filter being filled with an air-permeable sponge layer and/or an activated charcoal layer.

23. A handy oxygen generator according to claim 13, wherein said partition is made by heat-welding said sealed container.

24. A handy oxygen generator according to claim 13, wherein said partition is formed of a pressure-sealing zip-fastener.

25. A handy oxygen generator according to claim 1, wherein said inner reaction bag has gas permeability to allow only oxygen to pass therethrough.

* * * * *